United States Patent
Weinstein et al.

(10) Patent No.: US 6,382,205 B1
(45) Date of Patent: *May 7, 2002

(54) METHOD AND DEVICE FOR ORGANIZING AND COORDINATING THE COMBINED USE OF TOPICAL AGENTS FOR THE TREATMENT OF RESPIRATORY DISORDERS

(76) Inventors: Robert E. Weinstein, 177 Commonwealth Ave., Boston, MA (US) 02116; Allan M. Weinstein, 9205 Pegasus Ct., Potomac, MD (US) 20854

(*) Notice: Subject to any disclaimer, the term of this patent is extended or adjusted under 35 U.S.C. 154(b) by 0 days.

This patent is subject to a terminal disclaimer.

(21) Appl. No.: 09/432,133

(22) Filed: Nov. 2, 1999

(51) Int. Cl.[7] .............................................. A61M 11/00
(52) U.S. Cl. .......................... 128/200.23; 128/200.14; 128/203.12; 128/203.14; 206/534; 206/538; 206/828
(58) Field of Search ................... 128/200.23, 200.14, 128/203.14, 203.12; 206/534, 538, 828

(56) References Cited

U.S. PATENT DOCUMENTS

| | | | |
|---|---|---|---|
| 191,607 A | * 6/1877 | Millard | ....................... 312/209 |
| 4,039,080 A | 8/1977 | Cappuccilli | |
| 4,130,116 A | * 12/1978 | Cavazza | ...................... 128/203 |
| 4,553,670 A | 11/1985 | Collens | |
| 4,593,819 A | 6/1986 | Will | |
| 4,736,849 A | 4/1988 | Leonard | |
| 4,962,868 A | * 10/1990 | Borchard | ...................... 222/49 |
| 5,181,189 A | 1/1993 | Hafner | |
| 5,242,055 A | * 9/1993 | Pora | ........................... 206/532 |
| 5,377,841 A | 1/1995 | Varon | |
| 5,489,026 A | 2/1996 | D'Aloia | |
| 5,489,027 A | 2/1996 | Goerigk | |
| RE35,445 E | * 2/1997 | Pora | ........................... 206/532 |
| 5,755,462 A | * 5/1998 | Lupi | ........................... 283/56 |
| 5,830,490 A | 11/1998 | Weinstein et al. | |
| 5,941,241 A | 8/1999 | Weinstein et al. | |
| 6,076,520 A | * 7/2000 | Cooper | .................. 128/200.21 |

FOREIGN PATENT DOCUMENTS

FR    830269    5/1938

* cited by examiner

Primary Examiner—John G. Weiss
Assistant Examiner—Darwin P. Erezo
(74) Attorney, Agent, or Firm—Robert R. Deleault, Esq.; Mesmer & Deleault, PLLC

(57) ABSTRACT

A method and device for organizing, storing, instructing, and coordinating the combined use of topical therapeutic agents, including moisturizing agents, for the treatment of respiratory tract disorders.

13 Claims, 1 Drawing Sheet

METHOD AND DEVICE FOR ORGANIZING AND COORDINATING THE COMBINED USE OF TOPICAL AGENTS FOR THE TREATMENT OF RESPIRATORY DISORDERS

BACKGROUND OF THE INVENTION

1. Field of the Invention

The present invention relates to a method and device for organizing storing and coordinating the combined use of topical agents for the treatment of disorders including respiratory tract disorders for the purpose of reducing medication error and increasing therapeutic compliance.

2. Description of the Prior Art

Many drugs are utilized by patients over a period of time in varying amounts and in varying order to provide for their effective administration. Packaging has been developed for aiding the user of such drugs to comply with the proper administration over the proper time period. The dispensing apparatus associated with such multiple-day administrative drugs are typically directed to the administration of pills or capsules, or similar solid medication.

U.S. Pat. No. 4,039,080, for example, discloses a tray having individual compartments for pills which may contain a week's medication with indicia indicating the day of the week and time of the day the medication is to be taken.

U.S. Pat. No. 4,553,670 discloses another device comprising a support on which are located two different ingestible medicinal substances in a single dose form with an adjacent portion for instructional information.

U.S. Pat. No. 4,593,819 discloses a covered pill tray of rectangular configuration having an array of open-topped compartments to hold a supply of medication arranged by the day and time of taking the medication.

U.S. Pat. No. 4,736,849 discloses a method and another type of dispenser for the storage and dispensing of calendar-oriented pills.

U.S. Pat. No. 5,830,490 discloses an organizational tool for a lay person to organize topical medications together with oral medications into a single organizational treatment device with clear indicia and coordinated instructions and a method of reducing medication error and for enhancing compliance of combined topical/systemic modality therapeutic regimens.

U.S. Pat. No. 5,941,241 discloses an organizational tool for a lay person to organize combined topical medication regimens into a single organizational treatment device with clear indicia and coordinated instructions and a method of reducing medication error and for enhancing compliance of combined topical modality therapeutic regimens. This patent, however, does not disclose or include the incorporation of topical moisturizing and wetting agents in such devices and methods, nor include administration of topical agents by means other than aerosolization, such as by intranasal drops or lavage.

Therefore, what is needed is a device and method that incorporates topical moisturizing and wetting agents. What is further needed is a device and method that includes the administration of topical agents by means other than aerosolization.

SUMMARY OF THE INVENTION

Because the respiratory mucosa is structured as a conduit for air, it is possible to deliver medication topically to the respiratory mucosa. Often it is advisable for individuals suffering from respiratory tract disorders such as rhinitis, bronchitis, or asthma to utilize a combination of aerosols as a treatment regimen. Treatments that necessitate a multiplicity of topical components pose a number of problems for patients. Such multiple medication treatments may be a source of confusion and frustration that can result in medication error or lack of compliance.

The multiplicity of components may lack coordinating indicia and instructions for verifying the multiple component use together. Patients may confuse the various medications with one another. Individual components may be lost, misplaced, or ignored. This is particularly so with instructions issued separately from the medication. Without proper organization, the least used, least immediate acting, or least obvious acting components, even if important and offering enhanced long-term effect, are often the ones most likely to be lost or ignored. Furthermore, in spite of careful oral and written instruction from the health care provider, many patients are known to use what they have conveniently available.

These haphazard applications not only result in treatment failure, but also result in further expense for the patient. The patient will eventually have to seek additional professional medical consultation. This involves additional medical personnel time and expense to instruct and organize therapy for these individuals. Additionally, cost factors and outcomes are now being carefully considered by medical groups.

There is a need for devices and methods of the present invention which help patients be more cognizant of their proper medication treatment and therapy regimens. The present invention improves and fosters patient compliance. The present invention provides not only a means of further instruction but also provides an organizational tool that can save additional medical personnel expenditures. Successful therapy is less costly than unsuccessful treatment. Unsuccessful treatment eventuates in prolonged illness, multiple illnesses, multiple clinic visits, or hospitalizations. The devices and methods of the present invention greatly help overcome these noted problems.

It is an object of the present invention to provide a system that will help patients be more aware of their medication treatment and therapy regimens. It is a further object of the present invention to improve and ensure patient compliance. It is still a further object of the present invention to provide a system that incorporates topical moisturizing and wetting agents. It is yet a further object of the present invention to include instructions and administration of topical agents by means other than aerosolization.

The present invention achieves these and other objectives by providing a system for the treatment of respiratory disorders that require a combined topical agent regimen and a method for reducing medication error and enhancing therapeutic compliance of combined topical agents for treatment of such disorders. The system includes a unifying dispensing container that is prepackaged for a user. The unifying container holds at least two topical agents in multi-dosage units, indicia for distinguishing these agents and instructions for their coordinated use together as a single therapeutic regimen. Spacer devices and apparatus to measure outcomes of using the topical agents may also be included. Multi-dosage unit means more than one dosage of the contained agent is available within the unit. The present invention also includes a method of reducing medication error and enhancing therapeutic compliance of combined topical agents for treatment of respiratory disorders. The method includes obtaining a prepackaged, unifying container of the present invention and utilizing the topical agents according to the administration instructions incorporated within the prepackaged container.

DETAILED DESCRIPTION OF THE PREFERRED EMBODIMENT

Figure 1:
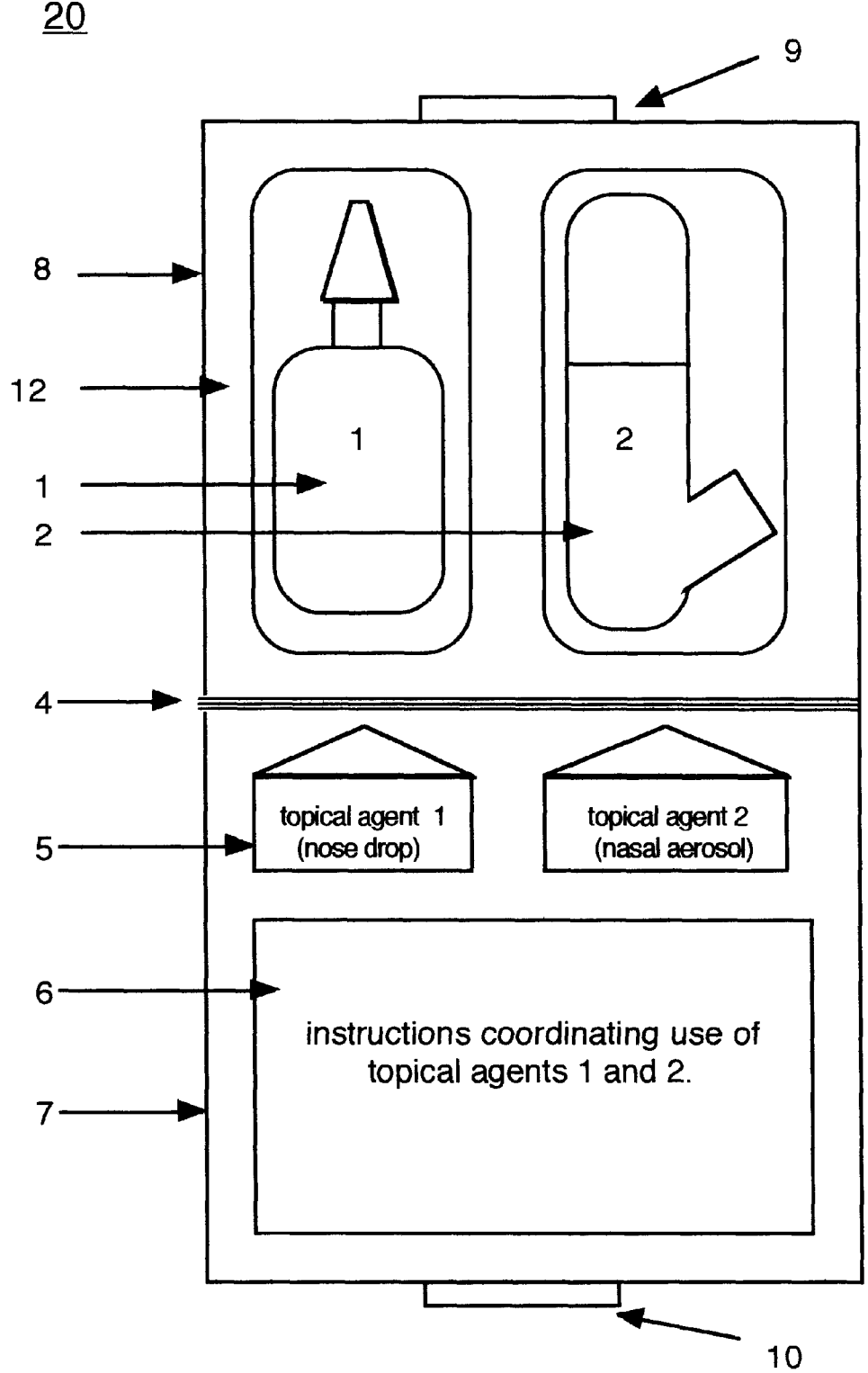
FIG. 1 is a plan view of a container in accordance with the present invention.

The following detailed description of the invention is provided to aid those skilled in the art in practicing the present invention, however, it should not be construed to unduly limit the present invention. Variations and modifications in the disclosed embodiments may be made by those of ordinary skill in the art without departing from the scope of the present invention. With regard to the drawings, it will be understood that while preferred embodiments of the invention have been illustrated and described, the invention is not limited to such embodiments. Changes and additions may be made without departing from the spirit of the invention.

The present invention provides a unifying dispensing container for therapeutic agents for treatment of respiratory disorders which require a combined topical agent regimen and a method for reducing medication error and enhancing therapeutic compliance of combined topical agents for treatment of such disorders. The unifying container holds at least two topical agents in multi-dosage units, indicia for distinguishing these agents, and instructions for their coordinated use together as a single therapeutic regimen. Spacer devices and apparatus to measure outcomes of using the topical agents may also be included. It is to be understood that by multi-dosage unit it is meant that more than one dosage of the contained agent is available within the unit. Such multi-dosage units may contain and facilitate the application of multiple doses of the therapeutic agent preferably by aerosolization, and/or by other means of topically applying therapeutic agents as is known in the art, such as in liquid form as exemplified by drops or lavages, or in semi-solid form as exemplified by creams, and ointments. The word aerosolization encompasses its ordinary dictionary meaning of a providing a suspension of fine solid or liquid particles in air or gas.

Detailed embodiments of the invention have been described in the aforementioned U.S. Pat. No. 5,941,241 which disclosure is incorporated herein by reference in its entirety. An additional embodiment is depicted in FIG. 1.

FIG. 1 depicts a topical respiratory treatment system 20 in a support package 12. Support package 12 has a first portion 7 and a second portion 8. Second portion 8 houses dosages of a first topical agent 1 and a second topical agent 2. A fold 4 in the package is provided in the center between first portion 7 and second portion 8. Identifying indicia 5 is provided with respect to first topical agent 1 and second topical agent 2. Identifying indicia 5 may be provided on first portion 7 or second portion 8, or on the immediate package of the agents, or on the agents themselves such as by color, shape, size, etc. First portion 7 houses an instruction-bearing portion 6 that provides instructions coordinating use of first topical agent 1 and second topical agent 2 as a regimen. The first portion 7 and the second portion 8 of the support package each contain respective clasp portions 9 and 10 which can be secured together when support package 12 is folded along fold 4. Other containers, such as a conventional folding paper box, and other closures are within the scope of the invention.

Topical agents that are presently used in combination for the treatment of respiratory disorders have been previously disclosed in U.S. Pat. No. 5,830,490. These include corticosteroids, decongestants, antihistamines, cell stabilizers, broncho-dilating adrenergic agents, and anticholinergic agents. What has not previously been disclosed is the inclusion of topical moisturizers. Topical moisturizers are utilized to moisten dry nasal membranes, loosen or thin nasal secretion and lavage the nasal cavity to remove mucous and inflammatory secretions from the nasal passages and/or sinuses.

Topical nasal moisturizers and washes may be formulated so as to be isotonic, hypotonic, or hypertonic with respect to saline. Examples of marketed topical nasal moisturizers include NaSal™ Moisturizer which contains sodium chloride 0.65%, benzalkonium chloride and thimerosal 0.001% as preservatives, mono- and dibasic sodium phosphates as buffers and purified water, and AYR Saline Nasal Mist and Drops which contain buffered isotonic saline adjusted to pH and topicity with monobasic potassium phosphate/sodium hydroxide buffer, and similarly preserved. It may be considered desirable to modify or eliminate the inclusion of preservatives. Other examples of agents used to moisten membranes are the wetting agents propylene glycol and polyethylene glycol.

The invention will be further clarified by a consideration of the following examples, which are intended to be purely exemplary of the invention.

EXAMPLE 1

Topical Intranasal Agents including a Moisturizing Agent and a Corticosteroid

One beneficial treatment regime includes the use of topical nasal saline aerosol or drops to relieve nasal dryness and help moisten and remove thick secretions, followed by a topical intranasal corticosteroid aerosol to reduce inflammation. One advantage of using the saline moisturizer first is to clear the nasal passages for improved dispersion of the anti-inflammatory corticosteroid. A medication regimen exemplifying this includes: Ocean Mist™ Buffered Saline, two sprays in each nostril four times a day, followed by Flonase® Nasal Spray, one spray in each nostril twice a day.

EXAMPLE 2

Topical Intranasal Agents including a Decongestant and a Moisturizing Agent.

Another beneficial treatment regime includes the use of a topical nasal decongestant in the form of aerosol or drops to shrink the nasal membranes and open the nasal and sinus passages, followed by a topical intranasal moisturizing agent to moisten and remove thick secretions and relieve nasal dryness. A medication regimen exemplifying this includes: Neo-Synepherine Nasal Spray® (phenylephrine hydrochloride) decongestant two sprays in each nostril four times a day followed by Ocean Mist™ Buffered Saline, two sprays in each nostril four times a day. Examples of other topical decongestants include oxymetazoline and ephedrine solutions. Topical nasal decongestants are preferably utilized for a five-day period or less.

Examples of more complex regimens that limit the use of decongestant are:

(a) a five day course of decongestant and moisturizer, followed by moisturizer alone thereafter, or (b) a five-day course of decongestant alone followed by moisturizer thereafter.

These examples are not inclusive and other variations may occur to those skilled in the art, which are within the scope of the invention set forth in the appended claims. Those skilled in the art may also recognize modifications to these presently disclosed embodiments. These variations and modifications are meant to be covered by the spirit and scope of the present claims.

What is claimed is:

1. A prepackaged therapeutic device for reducing medication error and enhancing therapeutic compliance of combined topical treatments, said therapeutic device comprising:

at least two topical multi-dosage therapeutic agents, including a moisturizing agent;

coordinating instructions for said at least two topical agents for use together as a single therapeutic regimen, said coordinating instructions including frequency of dosing and number of applications at each time of dosing for said at least two topical agents;

indicia for indicating and distinguishing said at least two topical agents; and a unifying container structured to provide placements for said at least two topical agents, said coordinating instructions and said indicia.

2. The device of claim 1 wherein said at least two topical agents are selected from the group consisting of corticosteroids, decongestants, antihistamines, cell stabilizers, broncho-dilating adrenergic agonists, anticholinergic agents and moisturizing agents.

3. The device of claim 1 wherein one of said at least two topical agents is devised for aerosol administration.

4. The device of claim 1 wherein one of said at least two agents is devised for administration as drops.

5. The device of claim 1 wherein said indicia is located on at least one surface of said unifying container and said at least two topical agents for distinguishing said at least two topical agents.

6. A prepackaged, medicament dispensing container for combined topical treatments, comprising:

at least two topical multi-dosage therapeutic agents, including a moisturizing agent;

indicia on at least one surface of said container and said at least two topical agents for distinguishing said at least two topical agents; and instructions for coordinating said at least two topical agents for use together as a single therapeutic regimen, said instructions including frequency of dosing and number of applications at each time of dosing.

7. The container of claim 6 wherein said at least two topical agents are selected from the group consisting of corticosteroids, decongestants, antihistamines, cell stabilizers, broncho-dilating adrenergic agonists, anticholinergic agents and moisturizing agents.

8. The container of claim 6 wherein one of said at least two topical agents is devised for aerosol administration.

9. The container of claim 6 wherein one of said at least two topical agents is devised for administration as liquid drops.

10. A method of reducing medication error and enhancing therapeutic compliance of combined topical treatments, comprising the step of:

utilizing a combined topical therapeutic regimen contained within a unified device, comprising:

at least two topical multi-dosage therapeutic agents, including a moisturizing agent;

coordinating instructions for using said at least two topical agents for use together as a single therapeutic regimen, said coordinating instructions include frequency of dosing and number of applications at each time of dosing for said at least two topical agents;

indicia for indicating and distinguishing said at least two topical agents; and a unifying container structured to provide placements for said at least two topical agents, said coordinating instructions and said indicia.

11. The method of claim 10 wherein said topical therapeutic agents are selected from the group consisting of corticosteroids, decongestants, antihistamines, cell stabilizers, broncho-dilating adrenergic agonists, anticholinergic agents and moisturizing agents.

12. The method of claim 10 wherein one of said at least two topical agents is devised for aerosol administration.

13. The method of claim 10 wherein one of said at least two topical agents is devised for administration as liquid drops.

* * * * *